US007995214B2

United States Patent
Forster et al.

(10) Patent No.: US 7,995,214 B2
(45) Date of Patent: Aug. 9, 2011

(54) APPARATUS AND METHOD FOR RECORDING THE SHAPE OF AN EAR SECTION

(75) Inventors: Frank Forster, München (DE); Rudolf Holzner, Altdorf (DE); Martin Kunz, München (DE); Uwe Rass, Nürnberg (DE); Anton Schick, Velden (DE)

(73) Assignee: Siemens Medical Instruments Pte. Ltd., Singapore (SG)

( * ) Notice: Subject to any disclaimer, the term of this patent is extended or adjusted under 35 U.S.C. 154(b) by 0 days.

(21) Appl. No.: 12/844,087

(22) Filed: Jul. 27, 2010

(65) Prior Publication Data
US 2011/0026037 A1 Feb. 3, 2011

Related U.S. Application Data

(60) Provisional application No. 61/229,043, filed on Jul. 28, 2009.

(51) Int. Cl.
*G01B 11/24* (2006.01)
(52) U.S. Cl. ....... 356/601; 356/600; 381/322; 381/73.1; 381/345
(58) Field of Classification Search .......... 381/322–329, 381/354, 73.1, 162, 345; 356/600–601
See application file for complete search history.

(56) References Cited

U.S. PATENT DOCUMENTS

| 5,837,782 A | 11/1998 | Sanchez |
| 2003/0164952 A1 | 9/2003 | Clausen |
| 2007/0112273 A1* | 5/2007 | Rogers ........................ 600/475 |
| 2009/0018465 A1 | 1/2009 | Hessel et al. |
| 2010/0060718 A1* | 3/2010 | Forster et al. ................. 382/154 |

FOREIGN PATENT DOCUMENTS

| WO | 2008058882 A1 | 5/2008 |
| WO | WO 2008092820 A1 | 8/2008 |

* cited by examiner

*Primary Examiner* — Gregory J Toatley
*Assistant Examiner* — Iyabo S Alli

(57) ABSTRACT

An apparatus for recording a shape of a section of the human ear is provided. The apparatus has a recording device for recording a spatial shape of a first and a second subsection of the section and for recording a position or a variable representing the position of the first and the second subsection relative to a predetermined optical feature of the section. The apparatus has an evaluation device for obtaining shape information about the section by combination of the shapes of the subsections based on the recorded positions or the variables representing the respective position. This enables a number of individual images to be joined together into a three-dimensional map based on natural features in the auditory canal, such as skin flecks or veins for example.

15 Claims, 1 Drawing Sheet

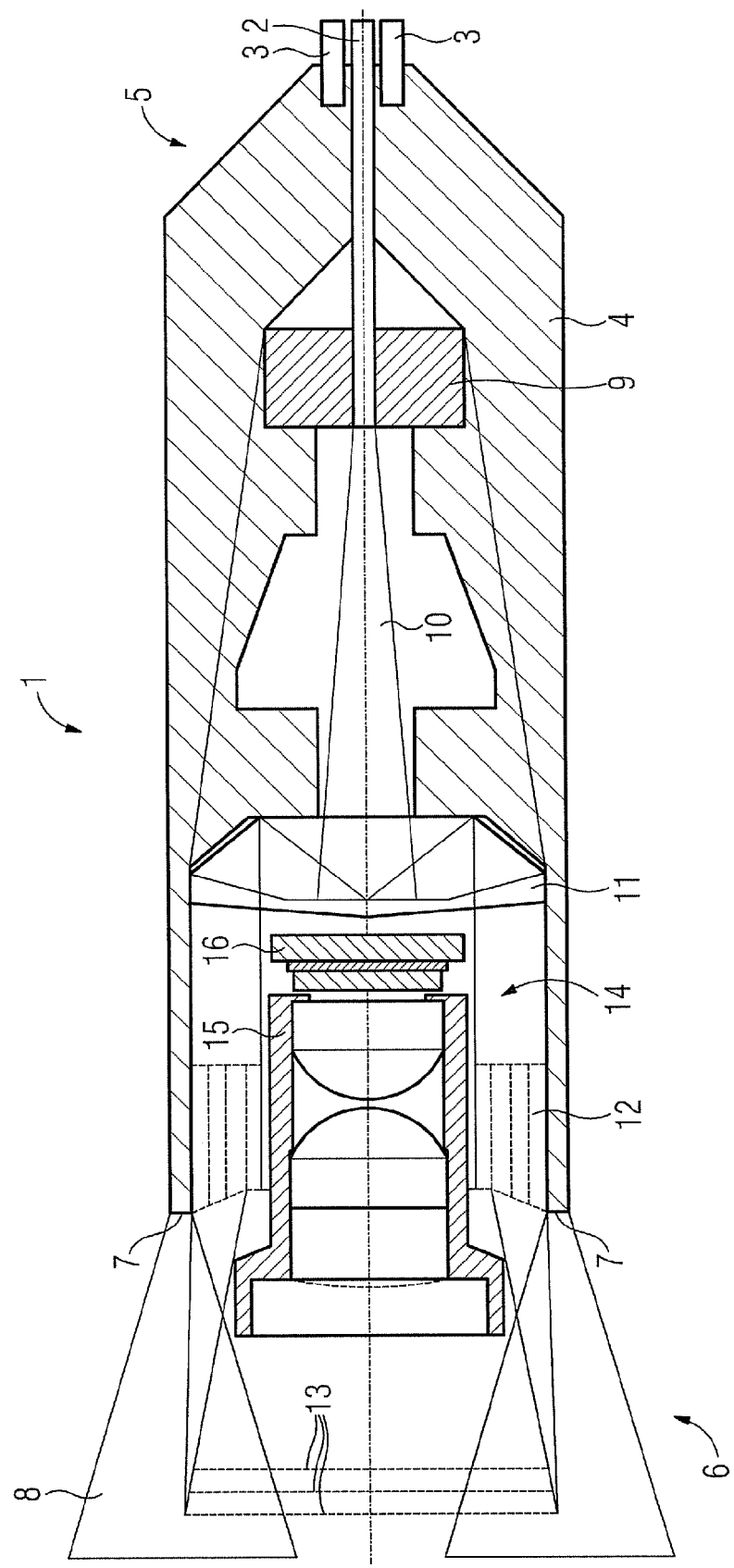

APPARATUS AND METHOD FOR RECORDING THE SHAPE OF AN EAR SECTION

CROSS REFERENCE TO RELATED APPLICATIONS

The present application claims the benefit of a provisional patent application filed on Jul. 28, 2009, and assigned application No. 61/229,043, which is incorporated by reference herein in its entirety.

FIELD OF THE INVENTION

The present invention relates to a device for recording the shape of a section of a human ear, especially of an auditory canal. In addition the present invention also relates to a corresponding method for recording an ear section.

BACKGROUND OF THE INVENTION

To manufacture individual otoplastics for in-the-ear-hearing devices it is necessary to precisely measure or determine the three-dimensional shape of an individual auditory canal.

Previously the shape of an auditory canal was typically recorded by silicon material being injected into the auditory canal. The material hardens after a few minutes. Subsequently the material is taken out of the auditory channel and scanned in order to obtain 3D data. However this procedure is unpleasant for patients and is labor-intensive overall.

A method for generating structured light is known from the publication with the application number PCT/EP2008/050929.

SUMMARY OF THE INVENTION

The object of the present invention is to simplify the manufacture of individual hearing device otoplastics and make designing them more convenient. In particular the determination of the three-dimensional shape of an auditory canal is to be improved.

Inventively this object is achieved by an apparatus for recording the shape of a section of a human ear, especially an auditory canal, comprising a recording device for recording a spatial shape of a first and at least one second subsection of the section to be recorded and for recording a variable representing a position in each case of the first and at least one second subsection relative to a predetermined optical feature of the section to be recorded, such as for example positions of natural features such as veins, pores etc., and also an evaluation device for obtaining shape information about the section to be recorded by combination of the shapes of the subsections based on their variables representing the respective position.

In addition the invention provides a method for recording the shape of a section of a human ear, especially an auditory canal, by recording a spatial shape of a first and at least one second subsection of the section to be recorded and recording a variable representing a position in each case of the first and at least second subsection relative to a predetermined optical feature of the section to be recorded, such as for example positions of natural features such as veins, pores etc., and also obtaining shape information about the section to be recorded by combination of the shapes of the subsections based on their recorded positions or their variables representing the respective position.

In an advantageous manner it is possible by recording one or more optical features on an ear to align a number of measurement recordings exactly to one another and thus to obtain a three-dimensional shape of a section of the ear and especially of the auditory canal. Above all an impression of the ear no longer has to be obtained by injecting material into the ear.

Preferably the recording device has a laser measurement arrangement with which a measurement beam in the shape of the surface of a cone is able to be created. This enables an annular subsection of the ear or auditory canal to be measured by triangulation.

In particular the laser arrangement enables a number of measurement beams in the shape of a cone surface to be generated simultaneously. This allows a number of subsections of the ear or of the auditory canal to be recorded simultaneously.

The wavelength of the laser beam of the laser measurement arrangement preferably lies in the blue area of the spectrum. This produces a small penetration depth or a favorable scatter characteristic of the skin.

In a preferred embodiment the laser intensity of the laser measurement arrangement is regulated as a function of the reflected amount of light. This enables more accurate measurements to be obtained.

In accordance with another development a number of predetermined optical features of the section to be recorded can be detectable. This typically enables the movement of the detection device to the better determined and the individual recordings to be added to one another with greater accuracy in order to obtain a three-dimensional image.

Furthermore the detection device can have an illumination device for diffuse illumination of the section to be recorded. The separately provided illumination device enables the optical features to be better recorded.

Advantageously the detection device is embodied as a cylinder and has a diameter of less than 10 mm, preferably less than 5 mm, so that it is able to be moved axially in an auditory canal. This enables precise mapping of the auditory canal to be achieved. In particular it is of advantage here for the recording device to be introduced into the auditory canal before the recording and to be moved out of the auditory canal for recording. On the basis of the optical feature or features one or more movement vectors are then determined, with the aid of which the individual recordings are combined.

BRIEF DESCRIPTION OF THE DRAWINGS

The present invention will now be explained in greater detail with reference to the enclosed drawing which shows a cross-section through a recording device of an inventive apparatus for recording the shape of a section of the human ear.

DETAILED DESCRIPTION OF THE INVENTION

The exemplary embodiments explained in greater detail below represent preferred exemplary embodiments of the present invention.

The recording device shown in the FIGURE represents the optical part of an inventive facility, for obtaining 3D data of an auditory canal for example. The recording device 1 is embodied here in the shape of the cylinder and has a diameter of just a few millimeters (e.g. 2 or 3 mm). It is thus able to be moved freely in a typical human auditory canal at least in the axial direction. The recording device 1 is connected in the present example with the aid of an optical fiber 2 to a laser which generates the light for the measurement beam. Furthermore the recording device is typically connected by plastic optical waveguides 3 to an illumination source which supplies the light for recording optical features in the auditory canal. In the example described the illumination source and the laser are located outside the recording device, but they can alternately also be integrated into the device.

In addition the inventive apparatus has an evaluation device not shown in the FIGURE to determine 3D data of the auditory canal from the images (of the subsections) obtained. The evaluation device is preferably connected via an electrical cable (likewise not shown) to the recording device 1. This means that the recording device 1 is able to be moved in the auditory canal independently of the evaluation device and if necessary also independently of the light sources.

The recording device 1 shown in the FIGURE has a transparent, roughly cylindrical shaped body 4 which, in addition to its light guiding function, also performs the function of a housing. The right-hand end face side of this transparent body 4 can be referred to as the supply side 5, into which light is injected via the optical waveguide 3 or the glass fiber 2. The opposite end face side of the transparent body 4 can be referred to as the recording side 6 since the light necessary for the measurements exits from this side and reflected beams are recorded.

From the plastic optical waveguides 3 white light is conveyed directly into a supply-side section of the transparent body 4. This section of the transparent body 4 is shaped and embodied so that light in the radially outlying areas of the transparent body is guided in the direction of the recording side 6. On the recording side 6 the transparent body 4 is arranged in the shape of a ring so that an annular exit surface 7 is produced for the white light. There the white light exits and forms a diffusely spread-out illumination ring 8. It is used for illuminating the wall of the auditory canal in order to be able to record optical features such as flecks, veins or small hairs on the skin.

The glass fiber 2, which introduces the laser light into the recording device 1 initially runs through the supply-side section of the transparent body 4 and ends in a ferrule 9, which aligns and fixes the end of the glass fiber in the transparent body 4. The glass fiber 2 runs exactly on the axis of the transparent body 4. The laser beam 10 emerging from the end of the glass fiber hits what is known as an axicon lens 11. There it is widened out into an annular cross-section and collimated. In this form it hits a ring projection lens 12 which splits up the laser light here into three bundles which are thrown against the wall of the auditory canal. This produces three laser rings 13 on the auditory canal wall.

A camera 14 arranged within the ring projection lens 12 possesses a wide-angle lens 15 here, with which the reflected light can be recorded within a wide-angle (for example up to 45°). The recorded or picked up light is projected onto a camera chip 16. The camera 14 thus enables both optical features on the auditory canal wall and also reflections of the laser rings 13 on the auditory canal wall to be recorded.

The function of the recording device 1 as well as the entire inventive scan apparatus is explained in greater detail below. As mentioned, the scan apparatus possesses the camera 14 for recording a series of images. In addition it has a light guide system to illuminate the auditory canal, a laser light guide system and an optical lens system 11 and 12 for projection of structured laser light (e.g. rings 13) onto the auditory canal wall. In respect of the generation of the structured light the reader is explicitly referred to document PCT/EP2008/050929.

The laser rings 13 mark those points on the auditory canal wall for which the distance information is obtained by triangulation. By moving the recording device out of the auditory canal the complete auditory canal wall is scanned. The individual images recorded by the camera 14 are aligned to one another with the aid of a localization of natural features of the auditory canal wall in three-dimensional space. These natural or optical features can be veins, flecks on the skin which are differentiated by their color from the surrounding auditory canal wall, pores and the like. However these features can also include small hairs which are present like the other natural features in the auditory canal.

To make possible the localization or tracing of the optical, natural features, the auditory canal is illuminated diffusely so that the camera 14 can detect these features. The features are finally recorded by means of image processing and followed on from image to image in order to obtain a movement vector of the camera 14. With this information the individual images are aligned to one another in order to obtain a three-dimensional point cloud as a model of the auditory canal. The number and quality of the features is determined in suitable software and the amount of light in the auditory canal is controlled or regulated accordingly.

The intensity of the laser beam is regulated as a function of the sharpness of the laser ring projection or of its reflection. With higher laser light intensity clearly measurable elements in deeper layers of the skin are also reflected so that the sharpness is reduced accordingly. The regulation thus allows an adaptive improvement of the accuracy of the individual recordings or measurements respectively.

The same measurement principle and the same measurement apparatus can be employed for scanning the ear muscle of a human ear. In this case the movement of the measurement or recording device is lateral, so that the projected laser rings travel across all sections to be scanned.

A specific form of embodiment of an inventive measurement device can be characterized by the fact that the diffuse illumination is undertaken simultaneously or alternately with the laser light irradiation. In accordance with a further exemplary embodiment the structured illumination (laser rings 13) can occur in the blue area of the spectrum. This blue illumination has advantages in relation to the penetration depth and the scatter characteristic on the skin. The diffuse illumination on the other hand is advantageously undertaken in the white area of the spectrum in order to enable the natural features to be better recognized. If the quality of the feature recognition is to be further improved a color camera can be used as the receive unit if necessary.

In the above example the light is generated in a separate functional unit and the light is supplied via optical waveguides 2, 3. As an alternative, as already indicated above, either one or all light sources (laser, LED) can also be contained in the recording device itself.

A further improvement can consist of the front lens of the camera 14 being formed in one piece with the ring projection lens. This component then has an illumination and an imaging function. The particular advantage of this form of embodiment lies in the fact that the recording device is then less sensitive to contamination (e.g. Cerumen). The one-piece optical element which forms the laser ring projection lens and if necessary a fisheye lens of the camera system especially also has advantages in production and system accuracy.

The evaluation device preferably uses a triangulation method to determine the desired distance information. This makes use of the fact that the angle of the laser beam and the observation beam in relation to the optical axis (axis of the recording device) and the distance between the two points at which the laser beam and the observation beam intersect the optical axis are known for the recording device used in each case.

The laser beam is scattered or reflected differently in the auditory canal. The scatter characteristic depends on the type of tissue of the auditory canal wall. Thus the type of scattered light can provide direct information as to where the bone material or soft tissue lie below the skin of the auditory canal. In soft tissue the laser penetrates more deeply below the skin than in more bony areas. This leads to different illumination gradients (i.e. sharper or wider, diffuse laser rings). Distinguishing between these areas of the auditory canal with a non-contact measurement method is important for the correct positioning of a hearing device. The information is also useful however for designing an otoplastic.

With the inventive measurement apparatus the three-dimensional shape of an auditory canal or of an ear muscle can thus be obtained without the use of auxiliary material. As a result of the localization of the natural features neither the absolute position of the measurement system nor the relative position to the head needs to be known. The position is merely calculated from the images, with the properties of the optical measurement system being known. These properties are determined during manufacturing by calibration procedure. This means that it is possible for an operator simply to manually move the system.

Typical focus of the eardrum or of the muscle can be included in order to determine the camera orientation (up or down). This is useful in order to obtain the correct orientation on a monitor without knowing how the camera was introduced into the auditory canal. This can also be achieved however by a position or acceleration sensor.

The diffuse illumination is achieved in the present example by the light being guided cylindrically around the camera by for example four central fibers so that a ring of light is formed on the measurement head. This has the advantage of enabling comparatively thick optical waveguides with low attenuation to be used. The laser light is also introduced centrally into the measurement head and guided around the camera in order to hit the ring projector lens, which creates the laser rings. This increases the stability of the measurement head.

The measurement facility can be used simultaneously as a video otoscope and a measurement facility. While the auditory canal is being observed 3D data is collected. The scanned parts can for example be marked in color on the screen of the video otoscope. This makes it possible to use the data of the scan for consultation and for the selection of a hearing device which typically occurs after an otoscopy (aural speculum).

The invention claimed is:

1. An apparatus for recording a shape of a section of a human ear, comprising:
    an optical waveguide connected to an illumination source that supplies light for recording a predetermined optical feature of the section;
    a recording device that records:
        a first spatial shape of a first subsection of the section and a second spatial shape of a second subsection of the section, and
        a first variable representing a first position of the first subsection and a second variable representing a second position of the second subsection relative to the predetermined optical feature of the section; and
    an evaluation device that combines the first spatial shape and the second spatial shape based on the first variable and the second variable.

2. The apparatus as claimed in claim 1, wherein the recording device comprises a laser measurement unit that creates a cone surface shape measurement beam.

3. The apparatus as claimed in claim 2, wherein the laser measurement unit simultaneously creates a plurality of cone surface shape measurement beams.

4. The apparatus as claimed in claim 2, wherein a wavelength of the laser measurement unit is in a blue area of a spectrum.

5. The apparatus as claimed in claim 1, wherein a laser intensity of the laser measurement unit is a function of a reflected amount of light.

6. The apparatus as claimed in claim 1, wherein the recording device records a plurality of predetermined optical features of the section.

7. The apparatus as claimed in claim 1, wherein the recording device comprises an illumination device that diffuses illumination of the section.

8. The apparatus as claimed in claim 1, wherein the recording device is a transparent cylinder having a diameter of less than 5 mm and a length of less than 15 mm to be moved axially in the section.

9. The apparatus as claimed in claim 1, wherein the section is an auditory canal of the human ear.

10. An apparatus for recording a shape of a section of a human ear, comprising:
    an optical waveguide connected to an illumination source that supplies light for recording a predetermined optical feature of the section;
    a recording device that records:
        a first spatial shape of a first subsection of the section and a second spatial shape of a second subsection of the section, and
        a first position of the first subsection and a second position of the second subsection relative to the predetermined optical feature of the section; and
    an evaluation device that combines the first spatial shape and the second spatial shape based on the first position and the second position.

11. A method for recording a shape of a section of a human ear, comprising:
    illuminating a wall of the human ear for recording a predetermined optical feature of the section by an optical waveguide connected to an illumination source;
    recording:
        a first spatial shape of a first subsection of the section and a second spatial shape of a second subsection of the section by a recording device, and
        a first position of the first subsection and a second position of the second subsection relative to the predetermined optical feature of the section or a first variable representing the first position and a second variable representing the second position by the recording device; and
    combining the first spatial shape and the second spatial shape based on the first position and the second position or the first variable and the second variable by an evaluation device.

12. The method as claimed in claim 11, wherein the recording device is introduced into the section before the recording and moved out of the section for the recording.

13. The method as claimed in claim 11, wherein a movement vector is determined based on the predetermined optical feature and the first spatial shape and the second spatial shape are combined based on the movement vector.

14. The apparatus as claimed in claim 1, wherein a recording side of the recording device is arranged in a ring shape for producing an annular exit for the light.

15. The apparatus as claimed in claim 1, wherein the predetermined optical feature comprises flecks, veins, or small hairs on a skin of the human ear.

* * * * *